United States Patent [19]
Bergen

[11] 4,009,964
[45] Mar. 1, 1977

[54] ATOMIC SPECTROSCOPY

[75] Inventor: Stephen Archbold Bergen, St. Ives, England

[73] Assignee: U.S. Philips Corporation, New York, N.Y.

[22] Filed: Aug. 4, 1975

[21] Appl. No.: 601,640

[30] Foreign Application Priority Data

Aug. 14, 1974 United Kingdom ............ 35776/74

[52] U.S. Cl. .................................. 356/85; 356/244; 356/246
[51] Int. Cl.[2] .................... G01J 3/30; G01N 21/16
[58] Field of Search ..................... 356/85, 244, 246; 250/341

[56] References Cited
UNITED STATES PATENTS

| | | | |
|---|---|---|---|
| 3,788,752 | 1/1974 | Slavin et al. | 356/85 |
| 3,858,980 | 1/1975 | West | 356/85 |
| 3,901,599 | 8/1975 | Meric | 356/85 |

OTHER PUBLICATIONS

"Laser–Microanalysis by Atomic Absorption," Mossotti et al., Spectrochimica Acta, 1967, vol. 23B, pp. 197–206.
"Vaporization of Elements . . . Discharge Lamps," Nelson et al, Spectrochimica Acta, 1963, vol. 19, pp. 781–784.

Primary Examiner—Vincent P. McGraw
Attorney, Agent, or Firm—Frank R. Trifari; Carl P. Steinhauser

[57] ABSTRACT

An atomic absorption spectroscopic apparatus employing a source of focused infra-red radiation and a holder for a sample at the focal point of the source of infra-red radiation in a chamber adapted to be purged by an inert gas and having windows transparent to a beam of monochromatic light, the holder being in path of the light beam.

5 Claims, 2 Drawing Figures

ATOMIC SPECTROSCOPY

This invention relates to apparatus for heating a sample of a substance to produce free atoms for atomic spectroscopy and to atomic spectroscopic apparatus including such heating apparatus, for example atomic absorption spectroscopic apparatus for automatic monitoring of liquid samples for trace elements.

In the known method of atomic absorption spectroscopy, the sample to be analysed is converted into free atoms in their ground state, the energy required for this transition being provided in the form of heat, usually in the region 2000°–2500° C. A beam of monochromatic light at the characteristic frequency of the atom to be detected is passed through the cloud of ground state atoms and is preferentially absorbed by them, the absorption being proportional to the number of atoms in the cross section of the beam. The source of the monochromatic light is typically a hollow cathode lamp, the cathode containing the element to be detected.

In instruments so far developed the source of the heat energy to reduce the atoms to their ground state is typically an air acetylene flame or a small carbon tube furnace directly heated to incandescence by an electrical current passing through it. Both these heat sources have the disadvantages of complexity and cost. In both the flame and carbon furnace methods, a large amount of excess heat is generated, which must be disposed of in the first case by ventilation and in the second by water cooling. Furthermore, in the flame method, noise and instability are produced in the measurement by physical disturbances of the flame and the chemical reactions within it.

An object of the invention is to provide means for producing free atoms which avoid the above mentioned disadvantages of the flame and carbon furnace.

According to the invention there is provided apparatus for heating a sample of a substance to produce free atoms for atomic spectroscopy, including a source of focussed radiant energy and means for holding a sample at the focal point of said source.

Preferably, said holding means includes a carrier element and means for moving the carrier element between a location where it can be loaded with a sample and said focal point. Furthermore, there can be provided a fixed cover element at said focal point which, when the carrier element is at said focal point, forms with the carrier element a cell to contain free atoms produced from a sample in the carrier element.

Automatic operation is sometimes desirable in atomic spectroscopy and so, according to the invention, there is further provided atomic spectroscopic apparatus.

Atomic absorption spectroscopy is particularly suitable for the analysis of trace elements of metals. An important example of this application is water pollution monitoring, where a simple and cheap means for providing automatic operation is particularly desirable.

An embodiment of the invention suitable for this application is atomic absorption spectroscopic apparatus for automatic monitoring of liquid samples for trace elements, including a chamber adapted to be purged by an inert gas and having windows transparent to a beam of monochromatic light; an infra red heater having a focal point within the chamber adjacent the path of said light beam; means for holding a liquid sample at said focal point, said holding means including a carrier element and means for moving the carrier element between a location within the chamber where it can be loaded with a liquid sample and said focal point; a fixed cover element at said focal point which, when the carrier element is at said focal point, forms with the carrier element a cell to contain within the path of said light beam free atoms produced from a sample in the carrier element; a syringe sampling mechanism for injecting a liquid sample through a septum in the chamber wall into the carrier element; and control means for moving the carrier element and the infra red heater.

This embodiment of the invention will now be described in more detail with reference to the drawing accompanying the provisional specification, in which.

Figure 1:
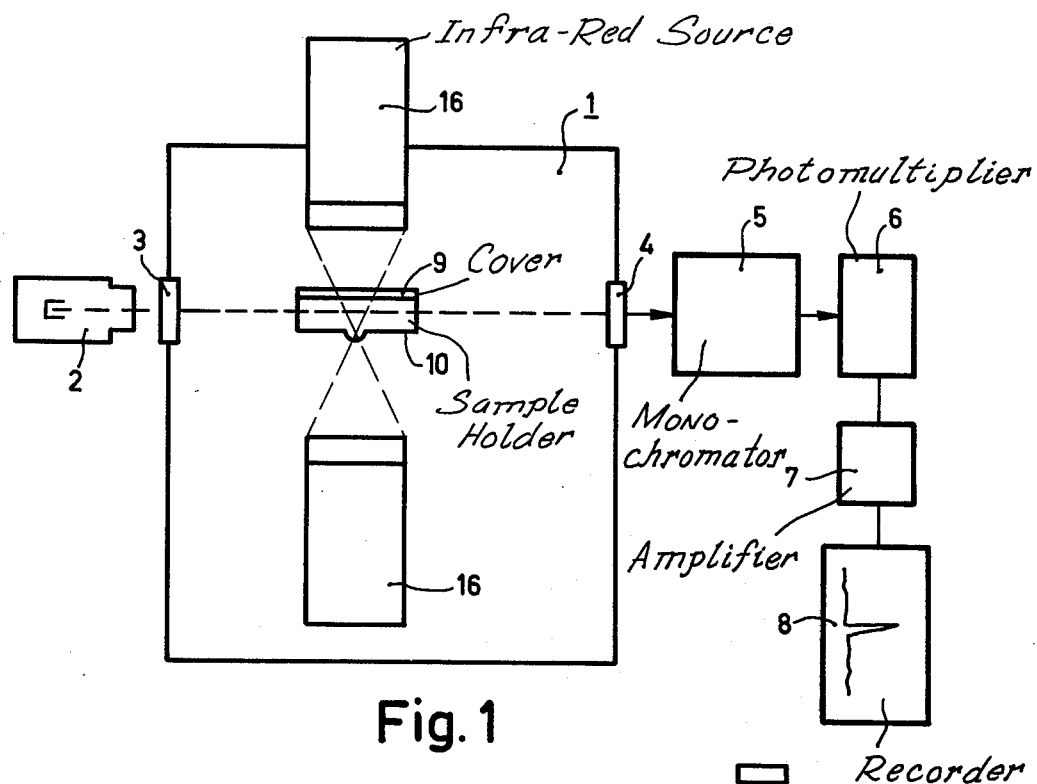
FIG. 1 shows a schematic diagram of an atomic absorption spectrometer.
Figure 2:
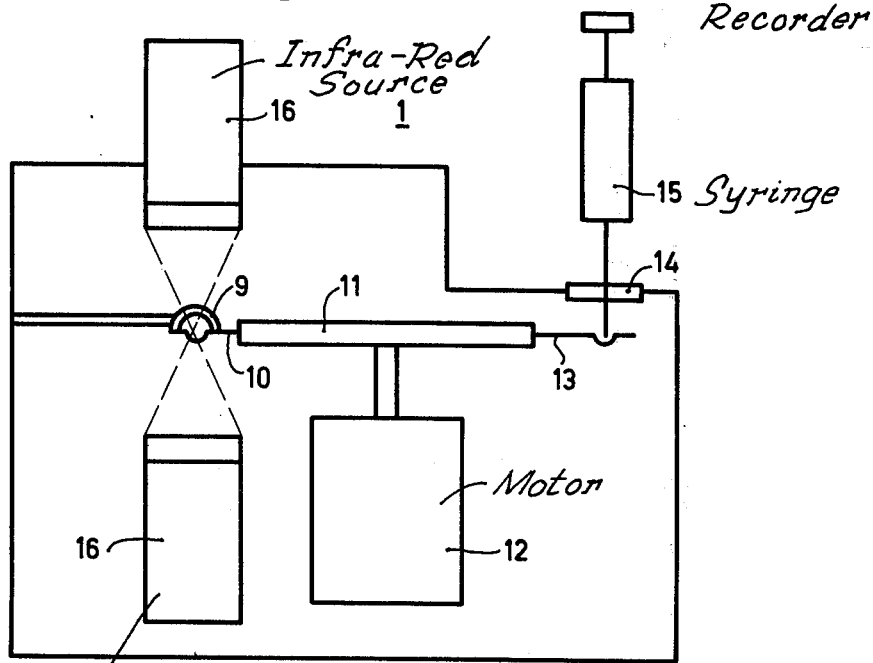
FIG. 2 shows a cross-section view of FIG. 2.

Referring now to the drawing, chamber 1 is capable of being purged by argon or other inert gas and is traversed by a beam of monochromatic light produced by a hollow cathode lamp 2 via windows 3 and 4. The beam of light then enters a monochromator 5, light from the exit slit of which is detected and measured by a photoelectricmultiplier 6. The signal from the multiplier 6 is amplified by an amplifier 7, and passed to a chart recorder 8.

Between windows 3 and 4 the beam of light passes through a cell in the form of a tunnel, the upper half of which is formed by a fixed channel section cover 9 which is made of transparent quartz and is mounted from the chamber 1.

The cover 9 is closed to form the tunnel cell by a carrier element 10, which has a dimple formed in it at its center to locate a liquid microsample. The sample carrier 10 is mounted on a disc 11, which is mounted on the shaft of, and rotated by, a motor 12 in a stepwise manner in conformance with a program on a time base. The programming system may be one of several known devices and is not illustrated here.

The disc 11 carries a number of carrier elements identical to the element 10, arranged so that, when one of them is in the position occupied by the element 10 in the drawing, another element 13 is in a loading position, that is directly under a sample injection system. This may be of several types, and by way of example, the one illustrated consists of a septum 14, made of a rubber-like material, through which is passed the needle of a hypodermic syringe 15, allowing a microsample of liquid to be injected into the dimple of sample carrier 13 without releasing the gas pressure in the chamber 1. The hypodermic syringe 15 may be either manually or automatically operated by means well known to practitioners of gas chromatography.

The sample carriers 10 and 13 are made of material which must be inactive chemically, capable of withstanding temperatures approaching 3000° C without serious de-formation, of low heat conduction and high heat absorbance. These conditions may be satisfied by such materials as silica, carbon or tantalum. In the latter two cases the thickness of the material must be small to reduce heat conduction away from the sample.

The dimple formed in the sample carrier 10 is at the focal point of one or more focussed sources of infra red radiation 16, such as a Philips Radiant Heat Gun type Z9600 which has a tungsten halogen filament with a focussing reflector.

The operation of the apparatus just described is as follows.

An accurately measured sample, typically of the order of 100 microlitres in size is introduced into the dimple in sample carrier 13 by means of the hypodermic syringe 15. The programming device rotates the sample carrier 13 via the motor 12 and disc 11 until it assumes the position shown for sample carrier 10, i.e. forming the base of a tunnel whose upper-half is made by the quartz channel 9.

The hollow cathode lamp 2 is switched on and the zero position of the recorder is established as the output of the detector 6 with the beam uninterrupted.

The radiant heat source or sources 16 are operated at low power for a short period to evaporate the solvent from the sample solution in the sample holder. Alternatively, the sample solution may be made to pass through the radiation of a separate infra red source, not illustrated, in passing from position 13 to position 10, so that the solvent is evaporated before it arrives there.

The dry sample is now subjected to a higher level of radiation from sources 16 to raise it to the atomisation temperature as rapidly as possible. In many cases, this will be between 2000°–2500° C. A cloud of free atoms will be produced in the tunnel cell formed by the carrier 10 and the cover 9, and will begin to diffuse towards the ends and the walls of the tunnel. The latter will be relatively cold since the transparent quartz channel 9 absorbs little radiation and does not rise to a high temperature. The rate of diffusion will be slowed down by the presence of the argon purge gas and for an appreciable time, a cloud of free atoms will exist in the tunnel, and will absorb a proportion of the monochromatic light passing through it. The absorption will rise to a maximum as the cloud of free atoms develops on the colder walls. The recorder will thus show a sharp peak of absorption, the maximum of which will correlate with the number of free atoms of the element to be monitored produced from the sample by the radiant heat. As the volume of the sample is accurately known, the concentration of the element in the solution can be calculated.

When atomisation of the sample has been completed, the radiation sources 16 are switched off, the disc 11 rotated to bring the next sample carrier under the channel section cover 9 and the cycle described above repeated.

The receiver output will thus be a series of sharp peaks whose height represents the concentration of the element to be monitored in a succession of samples.

What is claimed is:

1. Atomic absorption spectroscopic apparatus comprising a chamber adapted to be purged by an inert gas and having windows transparent to a beam of monochromatic light, a source of focussed infra-red radiation within said chamber having a focal point adjacent the path of said light beam and means for holding a sample at said focal point.

2. Apparatus as claimed in claim 1, in which said holding means includes a carrier element and means for moving the carrier element between a location where it can be loaded with a sample and said focal point.

3. Apparatus as claimed in claim 2, including a fixed cover element at said focal point which, when the carrier element is at said focal point forms with the carrier element a cell to contain free atoms produced from a sample in the carrier element.

4. Atomic spectroscopic apparatus including heating apparatus as claimed in claim 2, a sampling mechanism for loading a sample into the carrier element, and control means for programming the operation of the sampling mechanism, the means for moving the carrier element and the source of focussed radiant energy.

5. Atomic absorption spectroscopic apparatus for automatic monitoring of liquid samples for trace elements, including a chamber adapted to be purged by an inert gas and having windows transparent to a beam of monochromatic light; an infra red heater having a focal point within the chamber adjacent the path of said light beam; means for holding a liquid sample at said focal point, said holding means including a carrier element and means for moving the carrier element between a location within the chamber where it can be loaded with a liquid sample and said focal point; a fixed cover element at said focal point which, when the carrier element is at said focal point, forms with the carrier element a cell to contain within the path of said light beam free atoms produced from a sample in the carrier element; a syringe sampling mechanism for injecting a liquid sample through a septum in the chamber wall into the carrier element; and control means for programming the operation of the sampling mechanism, the means for moving the carrier element and the infra red heater.

* * * * *

UNITED STATES PATENT OFFICE
CERTIFICATE OF CORRECTION

Patent No. 4,009,964          Dated March 1, 1977

Inventor(s) Stephen A. Bergen

It is certified that error appears in the above-identified patent and that said Letters Patent are hereby corrected as shown below:

On the Title Page Section [73] should read

-- [73] Assignee: Pye Limited, Cambridge, England --.

Signed and Sealed this

Sixth Day of September 1977

[SEAL]

Attest:

RUTH C. MASON
*Attesting Officer*

LUTRELLE F. PARKER
*Acting Commissioner of Patents and Trademarks*